United States Patent
Copeland et al.

(10) Patent No.: US 6,441,209 B1
(45) Date of Patent: Aug. 27, 2002

(54) METHOD FOR TREATING ORGANIC ACID-TREATED PHOSPHATIDES

(75) Inventors: Dick Copeland; W. Maurice Belcher, both of Omaha, NE (US)

(73) Assignee: IP Holdings, L.L.C., Omaha, NE (US)

( * ) Notice: Subject to any disclaimer, the term of this patent is extended or adjusted under 35 U.S.C. 154(b) by 0 days.

(21) Appl. No.: 09/776,477

(22) Filed: Feb. 2, 2001

Related U.S. Application Data

(60) Continuation-in-part of application No. 09/550,375, filed on Apr. 14, 2000, now abandoned, which is a division of application No. 09/197,953, filed on Nov. 20, 1998, now Pat. No. 6,172,248.

(51) Int. Cl.$^7$ ................................................ C07F 9/02
(52) U.S. Cl. ............................................ 554/83
(58) Field of Search .......................................... 554/83

(56) References Cited

U.S. PATENT DOCUMENTS

| | | |
|---|---|---|
| 2,410,926 A | 11/1946 | Bush et al. |
| 4,036,865 A | 7/1977 | Hartmann et al. |
| 4,049,686 A | 9/1977 | Ringers et al. |
| 4,072,482 A | 2/1978 | Aoki et al. |
| 4,240,972 A | 12/1980 | Mag et al. |
| 4,698,185 A | 10/1987 | Dijkstra et al. |
| 4,713,155 A | 12/1987 | Arutjunian et al. |
| 4,996,072 A | 2/1991 | Marschner et al. |
| 5,696,278 A | 12/1997 | Segers |

FOREIGN PATENT DOCUMENTS

| | | |
|---|---|---|
| GB | 701633 | 12/1953 |
| GB | 714160 | 8/1954 |
| LU | 60116 | 12/1969 |
| NL | 18441 | 8/1928 |
| WO | WO 86/04603 | 8/1986 |
| WO | WO 94/12596 | 6/1994 |
| WO | WO 96/41852 | 12/1996 |

OTHER PUBLICATIONS

Patent Abstract of Japan, vol. 1997, No. 10, Oct. 31, 1997, JP 09 154504 (Asahi Denka Kogyo KK), Jun. 17, 1997.

Erickson, David R., *Degumming and Lecithin Processing and Utilization*, in Practical Handbook of Soybean Processing and Utilization 174, 179–80 (David R. Erickson ed. 1995).

J. C. Schmidt and F.T. Orthoefer, *Modified Lecithins*, in Lecithins 203, 206 (Bernard F. Szuhaj & Gary R. List eds., 1985).

Van Nieuwenhuyzen, W., Lecithin Production and Properties, *J. Amer. Oil Chem. Soc.* 53:425 (1976).

*Primary Examiner*—Deborah D. Carr
(74) *Attorney, Agent, or Firm*—McDonnell Boehnen Hulbert & Berghoff

(57) ABSTRACT

This invention relates to improved methods for treating organic acid-treated phosphatides. More particularly, this invention relates to improved methods comprising providing a phosphatide-containing material obtained from organic acid refining of vegetable oil, adjusting the pH of the phosphatide-containing material to form a neutralized phosphatide, and drying the neutralized phosphatide for a time sufficient to produce a dried phosphatide containing hydrolyzed lecithin.

10 Claims, 2 Drawing Sheets

METHOD FOR TREATING ORGANIC ACID-TREATED PHOSPHATIDES

CROSS-REFERENCE

This application is a continuation-in-part of U.S. patent application Ser. No. 09/550,375, filed Apr. 14, 2000, now abandoned, which is a divisional of U.S. patent application Ser. No. 09/197,953, filed Nov. 20, 1998 now U.S. Pat. No. 6,172,248.

FIELD OF THE INVENTION

This invention relates to improved methods for treating organic acid-treated phosphatides. More particularly, this invention relates to improved methods that comprise the steps of providing a phosphatide-containing material obtained from organic acid refining of vegetable oil, adjusting the pH of the phosphatide-containing material to form a neutralized phosphatide, and drying the neutralized phosphatide for a time sufficient to produce a dried phosphatide containing hydrolyzed lecithin.

BACKGROUND OF THE INVENTION

Phosphatides are one of several byproducts recovered during the purification of vegetable oil. Vegetable oils are typically obtained by pressing or extracting the oil seeds of plants such as corn or soybeans. Vegetable oils primarily consist of triglycerides, also termed triacylglycerols. In addition to triglycerides, however, vegetable oils also contain several other compounds. Some of these additional compounds, such as mono- and di-glycerides, tocopherols, sterols, and sterol esters, need not necessarily be removed during processing. Other compounds and impurities such as phosphatides, free fatty acids, odiferous volatiles, colorants, waxes, and metal compounds negatively affect taste, smell, appearance and storage stability of the refined oil, and hence must be removed. Carefully separated, however, some of these additional compounds, particularly the phosphatides, are valuable raw materials.

Vegetable oil triglycerides are esters of 1,2,3-propane triol, and can be represented by the generic formula

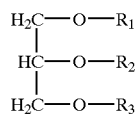

where $R_1$, $R_2$, and $R_3$ are the same or different, and are selected from the group consisting of $C_{10}$–$C_{22}$ saturated and unsaturated fatty acids. In soybean oil in particular, the saturated fatty acids that can occur include but are not limited to lauric (C12:0), myristic (C14:0), palmitic (C16:0), stearic (C18:0), arachidic (C20:0), and behenic (C22:0) acids. Generally, however, the fatty acids of soybean oil are predominantly unsaturated, and include but are not limited to oleic (C18:1), linoleic (C18:2), and linolenic (C18:3) acids. Unsaturated fatty acids can exist as geometric and/or positional isomers, each such isomer having different properties such as melting point. Naturally occurring fatty acids generally exist in the cis form, but they can be converted into the trans form during the course of purification steps used to produce a vegetable oil from an oilseed. Crude soybean oil in particular typically contains from about 95 to about 97 percent by weight triglycerides.

The terms phosphatides and phosphatide concentrates are commonly used to refer to a mixture of phospholipids comprising phosphatidyl derivatives which are present in crude vegetable oil. Such phosphatides also are referred to as gums. After being removed from vegetable oil by treatment with water, phosphatides are often called wet gums or wet lecithin. Upon being dried, phosphatides generally are termed lecithin or commercial lecithin. Crude soybean oil in particular provides the chief source for commercial lecithin.

The term lecithin, from a true chemical sense, refers to phosphatidyl choline. However, as used by commercial suppliers, the term lecithin refers to a product derived from vegetable oils, especially soybean oil. Specific chemical components of phosphatides present in vegetable oil include phosphatidyl choline, 1; phosphatidylethanolamine, 2; phosphatidylinositol, 3; phosphatidyl serine, 4; phosphatidic acid, 5; cyclolipids, and other components such as free sugars, metals and free fatty acids.

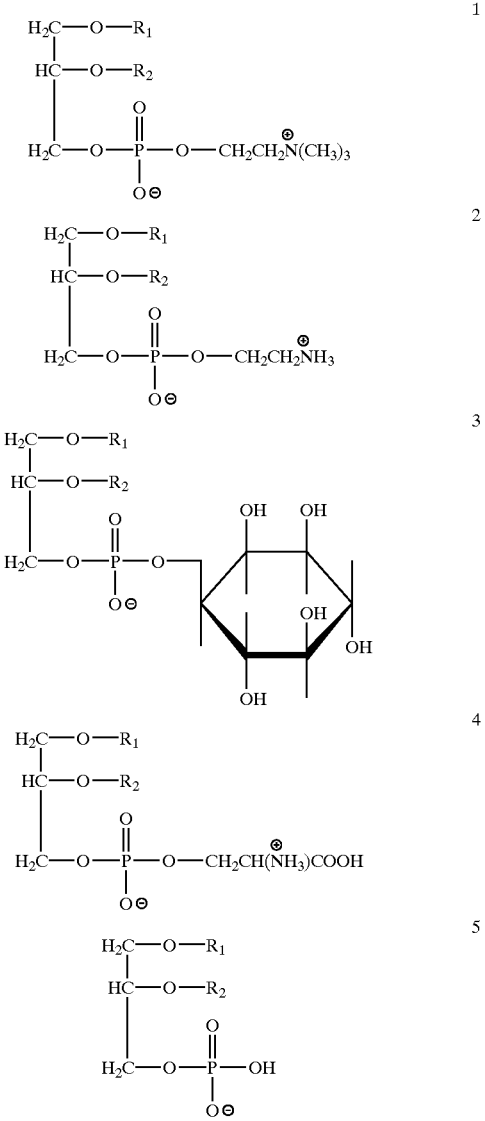

Such phosphatides are amphipathic, i.e. one end of the molecule is hydrophilic (lipophobic) and the other end is hydrophobic (lipophilic). As a result, they possess useful surface-active properties, and can orient in aqueous environments to create membranes and bilayers.

The fatty acid content of the phosphatides 1 through 5 is represented by $R_1$ and $R_2$, as defined above, and generally matches that of the vegetable oil from which the phosphatides are derived. The phosphatide content of vegetable oil will vary based on a number of factors, including but not limited to oilseed type, seed quality, and the process by which oil is extracted therefrom. Crude soybean oil in particular typically contains from about 1.5 to about 3 percent by weight phosphatides. Phosphatides comprise both hydratable phosphatides (HPs) and non-hydratable phosphatides (NHPs). Although non-hydratable phosphatides tend to remain oil-soluble and are largely unaffected by water, hydratable phosphatides when hydrated become greater in density than the triglycerides and precipitate, or settle out. This phenomenon forms the basis for the process of conventional water degumming, discussed more fully below.

Lecithin varies in appearance from highly viscous to semiliquid to powder, and generally is brown in color. Hydrolyzed lecithin, also termed lysolecithin or lysophosphatidylcholine (LPC), is a desirable modified form of lecithin and generally comprises a highly viscous or pasty fluid ranging in color from light brown to brown. The composition of several lecithins derived from vegetable oil is shown in Table 1. The fatty acid composition of lecithin derived from soybean oil in particular is shown in Table 2.

TABLE 1

Composition of Various Oil-Free Lecithins (%) Derived From Vegetable Oils

| Phosphatide Component | Soybean | Corn | Sunflower | Rapeseed |
|---|---|---|---|---|
| Phosphatidyl choline | 12–46 | 31 | 14 | 37 |
| Phosphatidyl ethanolamine | 8–34 | 3 | 24 | 29 |
| Phosphatidyl inositol | 1.7–21 | 16 | 13 | 14 |
| Phosphatidyl serine | 0.2–6.3 | 1 | — | — |
| Phosphatidic acid | 0.2–14 | 9 | 7 | — |
| Glycolipids | 14.3–29.6 | 30 | — | 20 |

TABLE 2

Fatty Acid Composition (% Range) of Lecithin Derived From Soybean Oil

| Fatty Acid | Percent by Weight |
|---|---|
| Palmitic | 11.7–42.7 |
| Stearic | 3.7–11.7 |
| Oleic | 6.8–39.4 |
| Linoleic | 17.1–60.8 |
| Linolenic | 1.6–9.2 |

Commercial lecithin is typically produced in a continuous process by drying phosphate concentrates, which are obtained as byproducts of vegetable oil purification processes, at a temperature of from 176° F. to 203° F. and at an absolute pressure of from about 50 mm Hg to about 300 mm Hg. Erickson, David R., *Degumming and Lecithin Processing and Utilization*, in Practical Handbook of Soybean Processing and Utilization 174, 179–80 (David R. Erickson ed. 1995); Van Nieuwenhuyzen, W., *J. Amer. Oil Chem. Soc.* 53:425 (1976). However, processing lecithin at high temperature risks increasing the concentration of objectionable volatile compounds, and further risks permanently fixing these objectionable compounds to the lecithin via chemical bonding.

Vegetable oil impurities are typically removed in four distinct steps of degumming, refining, bleaching, and deodorizing. Of these four steps, degumming removes the largest amount of impurities, the bulk of which are hydratable phosphatides. Refining primarily removes non-hydratable phosphatides, soaps created from the neutralization of free fatty acids, and other impurities such as metals. Bleaching then improves the color and flavor of refined oil by decomposing peroxides and removing oxidation products, trace phosphatides, and trace soaps. Soybean oil bleaching materials include neutral earth (commonly termed natural clay or fuller's earth), acid-activated earth, activated carbon, and silicates. Deodorizing is the final processing step and prepares the oil for use as an ingredient in many edible products including salad oils, cooking oils, frying fats, baking shortenings, and margerines. The deodorizing process generally comprises passing steam through refined oil at high temperature and under near vacuum conditions to vaporize and carry away objectionable volatile components.

Vegetable oil refining, also known as neutralization or deacidification, essentially involves removing free fatty acids (FFA) and phosphatides from the vegetable oil. Most refining operations employ either alkali refining (also termed caustic refining) or physical refining (also termed steam refining). Of these two refining methods, alkali refining predominates.

For either refining method, an optional but preferred first step is a conventional water degumming process. Degumming refers to the process of removing hydratable phosphatides and other impurities such as metals from vegetable oils. A simple degumming process comprises admixing demineralized water with the vegetable oil and separating the resulting mixture into an oil component and an oil-insoluble hydrated phosphatides component (frequently referred to as a "wet gum" or "wet lecithin"). The NHPs, generally considered to be calcium and magnesium salts of phosphatidic acids, are largely unaffected by water and remain soluble in the oil component. Phosphatidic acids are typically produced via the action of phospholipidases, which are released from the oil seed upon damage to the cellular structure.

Normally, refiners also must introduce chelating agents following degumming processes to remove metal compounds from crude vegetable oil, which typically contains calcium, potassium, magnesium, aluminum, iron and copper. Left in place, these metal impurities form salts of phosphatidic acid, thereby contributing to the NHP content. Moreover, metal contaminants, especially iron, can darken oil during deodorization, and even small amounts of iron that do not affect the oil's color can nevertheless dramatically reduce stability of refined oil.

Treating crude vegetable oil with demineralized water produces a degummed oil and a phosphatide concentrate containing the hydratable phosphatide fraction. This phosphatide concentrate subsequently can be removed from the degummed oil by a convenient method such as by gravitational force or by centrifugal separation. Phosphatide concentrates coming from centrifugal separation will generally contain up to about fifty percent by weight water, and typically will contain from about twenty-five to about thirty percent by weight water. In order to minimize chances of microbial contamination, phosphatide concentrates must be dried or otherwise treated immediately. Dried phosphatide concentrates can be profitably sold as commercial lecithin. Degummed oil is further refined to remove NHPs and other unwanted compounds.

Mineral acid also is sometimes added during the water degumming process to help minimize the NHP content of degummed oil. The acid combines with calcium and magnesium salts, enabling phosphatidic acids to migrate from the oil to the water phase, thus eliminating them from the crude oil. However, using mineral acid during degumming is inappropriate when seeking to recover gums intended for use as lecithin because the presence of mineral acid will cause darkening of the lecithin.

In alkali refining, free fatty acids and gums are removed from crude or degummed oil by mixing the oil with a hot, aqueous alkali solution, producing a mixture of so-called neutral oil and soapstock (also termed refining byproduct lipid), which is an alkaline mixture of saponified free fatty acids and gums. The neutral oil is then separated from the soapstock, typically by centrifugation. The soapstock has commerical value due to its fatty acid content but must be processed further in order to render it salable. The neutral oil is further processed to remove residual soap.

Soapstock is treated in a process called acidulation, which involves breaking or splitting the soap into separate oil and aqueous phases through addition of a mineral acid such as sulfuric acid to reduce the pH to approximately 1.5, followed by thorough heating and mixing. Because the aqueous phase is heavier than the oil phase, the acidulated soapstock is separated from the oil by gravity or centrifugation. The separated oil (termed acid oil) has essentially the composition of the neutral oil and is drawn off, washed with water to completely remove mineral acid and sludge, and sold, usually as an animal feed supplement. The remaining aqueous phase (termed acid water) is the final waste product and must be neutralized before being discarded.

The alkali refining process has several drawbacks, however. One drawback is that alkali refining allows recovering only the hydratable phosphatide fraction, because the non-hydratable phosphatide fraction is destroyed and converted into materials that wind up in the soapstock. And although employing mineral acids during water degumming can reduce the overall NHP content prior to alkali treatment by converting the NHPs into water-soluble forms, thus potentially increasing the percentage recovery of the overall phosphatide fraction, using mineral acids during degumming causes undesirable darkening of lecithin.

An alternative to alkali refining is physical refining. Physical refining is a steam distillation process essentially the same as that used in conventional vegetable oil deodorization processes, in which steam passing through vegetable oil vaporizes and carries away free fatty acids. The main advantage of physical refining over alkali refining is that no soapstock is generated. A second advantage is lower refining losses because there is no saponification of oil and no oil entrainment and/or emulsification by soapstock.

Accordingly, there is significant interest in physical refining due to its economic advantages and friendliness compared to alkali refining. But because physical refining does not remove NHPs, any oils to be physically refined must be free of NHPs in order to ensure stable refined oils. Oils such as palm oil and tallow, which have low NHP content, can be successfully physically refined. But oils such as soybean oil and sunflower seed oil, which are relatively high in NHPs, are not commonly physically refined because the pre-refining step of water degumming does not remove NHPs. Moreover, physically refined soybean oils have only limited acceptance in the U.S. market due to their lack of flavor stability.

One recent and attractive alternative route to obtaining phosphatide-containing mixtures is organic acid refining of vegetable oil, as disclosed in pending U.S. patent application Ser. No. 09/197,953. In an organic acid refining process, a dilute aqueous organic acid solution is admixed with a heated stream of crude vegetable oil to give an acid-oil blend. The acid-oil blend is thereafter subjected to high shear for a time sufficient to finely disperse the dilute aqueous organic acid solution in the crude vegetable oil and give an acid-and-oil mixture (also termed a phosphatide-containing mixture) and/or is subjected to low shear for a time sufficient to produce a phosphatide-enriched aqueous phase (also termed a hydrated impurities phase) into which oil contaminants are sequestered and also produce a purified vegetable oil phase.

Vegetable oils suitable for organic acid refining include but are not limited to those derived from soybean oil, corn oil, cottonseed oil, palm oil, peanut oil, rapeseed oil, safflower oil, sunflower seed oil, sesame seed oil, rice bran oil, coconut oil, canola oil, and mixtures thereof. A particularly preferred vegetable oil is soybean oil.

The dilute aqueous organic acid solution may be prepared from any food grade organic acid, including but not limited to phosphoric acid, acetic acid, citric acid, tartaric acid, succinic acid, or combinations thereof. A particularly preferred organic acid is citric acid. Using a food grade organic acid, as opposed to a mineral acid, ensures that phosphatides removed during the purifying process can be purified and sold as commercial lecithin to the food industry. Using an organic acid also enables sequestering metal contaminants without the need to add other chelating agents. In preparing the dilute aqueous organic acid solution, demineralized water is preferably used. Using demineralized water avoids the possibility of converting hydratable phosphatides to non-hydratable phosphatides. As used herein, the term demineralized water means water substantially devoid of calcium and magnesium ions.

The dilute aqueous organic acid solution has a concentration based on the combined weight of organic acid and water of from about 1 to about 5 percent by weight. The dilute aqueous organic solution is combined with the heated vegetable oil in a ratio of from about 3:97 to about 20:80, depending on the source from which the vegetable oil is derived and on whether the vegetable oil has been degummed.

The phosphatide-containing mixture generally comprises hydratable phosphatides, nonhydratable phosphatides that have been converted into water-soluble form, water, organic acid, and vegetable oil, as well as other contaminants including but not limited to metals. The phosphatide-containing mixture is mixed at low shear for a time of less than about 16 minutes to allow sequestering of contaminants, especially metals, into the phosphatide-enriched aqueous phase. The term sequestering as used herein refers to the process wherein contaminants are either directly or indirectly (through chemical conversion into water-soluble forms) taken up into the phosphatide-enriched aqueous phase.

In one mode of organic acid refining, the phosphatide-containing mixture is separated into its component parts in a stepwise fashion, the first step of which is separation into two streams comprising a purified vegetable oil phase and a phosphatide-enriched aqueous phase. Separation can occur by any convenient method, including by centrifugation or by permitting the phosphatide-containing mixture to settle for a time sufficient to develop a purified vegetable oil phase and a phosphatide-enriched aqueous phase. This route can be employed because the purified vegetable oil typically separates fairly quickly from the phosphatide-enriched aqueous phase. The purified vegetable oil phase can be further processed, as for example by bleaching and deodorizing, and subsequently used or sold. The phosphatide-enriched aqueous phase can be dried or it can undergo further processing.

The phosphatide-enriched aqueous phase itself comprises an aqueous organic acid phase and an organic acid-treated phosphatide phase. Accordingly, a second separation step can be used to isolate one of these two remaining phases from the other. Once isolated, the aqueous organic acid phase can be recycled without further treatment into the organic acid refining process. The organic acid-treated phosphatide phase can be further processed.

In another mode of organic acid refining, the phosphatide-containing mixture is separated directly into three component parts comprising a purified vegetable oil phase, an organic acid-treated phosphatide phase, and an aqueous organic acid phase. Separation advantageously occurs by permitting the phosphatide-containing mixture to remain unagitated for a time sufficient to develop discrete phases. Typically, the purified vegetable oil phase migrates to the top, the organic acid-treated phosphatide phase migrates to the middle, and the aqueous organic acid phase migrates to the bottom. Once discrete phases exist, they can be separated from each other in any order. Typically, however, the purified vegetable oil phase is separated first, and then one of the two remaining phases is separated from the other. As above, the purified vegetable oil phase can be further processed, as for example by bleaching and deodorizing, and subsequently used or sold. The aqueous organic acid phase can be recycled without further treatment into the organic acid refining process. The organic acid-treated phosphatide phase can be further processed.

Thus, alternate modes of organic acid refining produce either a phosphatide-enriched aqueous phase or a more concentrated organic acid-treated phosphatide phase, which, alone or in combination, can be further processed to produce lecithin. Lecithins are utilized in a broad variety of applications and perform an array of valuable functions. In edible compositions, lecithin contributes nutritional value and also can act as an emulsifying agent, surface-active agent, anti-spattering-agent, or stabilizing agent. Lecithin can be used in technical applications as an anti-foam agent, dispersing agent, wetting agent, stabilizing agent, and as an anti-knock compound for gasoline formulations. In particular, in foods such as baked goods or margarine, lecithin is used as a dispersing agent, emulsifier, viscosity reducer and antioxidant. In cosmetics such as shampoos or skin lotions, lecithin is employed as a foam stabilizer, emollient, emulsifier, and wetting agent. In pharmaceuticals targeted for either topical or parenteral administration, lecithin functions as softening agent, carrier, emulsifier, and penetration enhancer. Lecithin also possesses unique release properties, and is useful in pan-frying and pan grease formulations for baking, as well as in mold release formulations which enable casting forms to be easily removed.

If mistreated during drying, however, lecithin can have an objectionable odor and flavor that is difficult to remove. Phosphatides easily oxidize when subjected to heating, and such oxidative products can contribute a bitter or rancid taste to lecithin. Heating of phosphatides can also induce formation of volatile decomposition products such as 4,5-dimethylisoxazole, which contributes an objectionable flavor to lecithin. Other volatile compounds such as isophorone, a contributor of objectionable odor, can form by an aldol condensation reaction involving solvent remaining from crude vegetable oil refining processes. Thus, care must be exercised in the method used to remove objectionable volatile components from lecithin.

Changes in lecithin functionality and physicochemical properties can be made using various modification techniques. For example, fractionating lecithin in ethanol changes the ratio of phosphatidylcholine to phosphatidylethanolamine to produce a material having improved oil-in-water emulsifying ability. Acetytlation using acetic anhydride also improves oil-in-water emulsifying ability. Hydroxylation using hydrogen peroxide and lactic acid or a peracid improves oil-in-water emulsifying ability and water dispersibility. Hydrolysis of lecithin, normally achieved either via action of strong base or acid or via enzymatic action, provides a material having improved hydrophilic and emulsifying properties. Enzymatically modified lecithins incorporated into animal feed formulations can improve emulsification and digestibility of fats. In some animal studies, such hydrolyzed lecithins, also termed lysolecithins, were shown to be more rapidly absorbed following oral administration.

A typical acidic hydrolysis process for producing hydrolyzed lecithin comprises multiple processing steps of adding water and an acid such as hydrochloric acid to a dried lecithin, subsequently neutralizing with a base such as sodium hydroxide, and then redrying the lecithin. J. C. Schmidt and F. T. Orthoefer, *Modified Lecithins*, in Lecithins 203, 206 (Bernard F. Szuhaj & Gary R. List eds., 1985). However, such a process is inefficient because it requires drying, then rewetting, and then redrying. Moreover, because the most desirable hydrolyzed lecithin results when only one fatty acid is cleaved from the glyceride backbone, hydrolysis reactions employing strong acid or base can prove difficult to control in terms of halting the reaction at a desired point.

A typical enzymatic process for producing hydrolyzed lecithin comprises adding enzymes to a wet lecithin to catalyze conversion of the lecithin into a hydrolyzed lecithin. However, such enzymes are costly, and are often animal-derived, which can affect consumer acceptance. Moreover, enzymatic processes for producing hydrolyzed lecithin require that the enzymes be filtered out after lecithin conversion, adding further expense.

Thus, previously known methods for obtaining hydrolyzed lecithin have required complex and expensive processing steps. Consequently, further improvements in obtaining hydrolyzed lecithin have been sought. The present invention relates to improved processes having advantages over those previously disclosed. Surprisingly, the processes of the invention produce hydrolyzed lecithin directly and simply from either a phosphatide-enriched aqueous phase or an organic acid-treated phosphatide phase, both of which are obtained from an organic acid refining process.

SUMMARY OF THE INVENTION

One aspect of the present invention relates to an improved process that produces a dried phosphatide containing hydrolyzed lecithin from a phosphatide-containing material selected from the group consisting of a phosphatide-enriched aqueous phase obtained from an organic acid refining process, an organic acid-treated phosphatide phase obtained from an organic acid refining process, or a mixture thereof.

Another aspect of the invention relates to an improved process that produces a lecithin containing hydratable phosphatides and non-hydratable phosphatides that have been converted into water-soluble form. This aspect of the invention maximizes recovery of the overall phosphatide fraction contained in crude vegetable oil.

One embodiment of the invention is a process for treating an organic acid-treated phosphatide that comprises the steps of providing a phosphatide-containing material selected from the group consisting of a phosphatide-enriched aqueous phase obtained from an organic acid refining process, an organic acid-treated phosphatide phase obtained from an organic acid refining process, or a mixture thereof; adjusting the pH of the phosphatide-containing material to a value of from about 5 to about 7 to form a neutralized phosphatide mixture; and drying the neutralized phosphatide mixture for a time sufficient to convert the neutralized phosphatide mixture into a vapor phase and a dried phosphatide containing hydrolyzed lecithin.

Another embodiment of the invention is a process for treating an organic acid-treated phosphatide that comprises the steps of providing a phosphatide-containing material selected from the group consisting of a phosphatide-enriched aqueous phase obtained from an organic acid refining process, an organic acid-treated phosphatide phase obtained from an organic acid refining process, or a mixture thereof; adjusting the pH of the phosphatide-containing material to a value of from about 5 to about 7 to form a neutralized phosphatide mixture; drying the neutralized phosphatide mixture for a time sufficient to convert the neutralized phosphatide mixture into a vapor phase and a dried phosphatide containing hydrolyzed lecithin; and discharging the dried phophatide at a temperature of less than about 150° F.

Yet another embodiment of the invention is a process for treating an organic acid-treated phosphatide that comprises the steps of providing a phosphatide-containing material selected from the group consisting of a phosphatide-enriched aqueous phase obtained from an organic acid refining process, an organic acid-treated phosphatide phase obtained from an organic acid refining process, or a mixture thereof; adjusting the pH of the phosphatide-containing material to a value of from about 5 to about 7 to form a neutralized phosphatide mixture; bleaching the neutralized phosphatide mixture; and drying the neutralized phosphatide mixture for a time sufficient to convert the neutralized phosphatide mixture into a vapor phase and a dried phosphatide containing hydrolyzed lecithin.

Still another embodiment of the invention is a process for treating an organic acid-treated phosphatide that comprises the steps of providing a phosphatide-containing material selected from the group consisting of a phosphatide-enriched aqueous phase obtained from an organic acid refining process, an organic acid-treated phosphatide phase obtained from an organic acid refining process, or a mixture thereof; allowing the phosphatide-containing material to remain at acidic pH for a time of no more than about 8 hours; adjusting the pH of the phosphatide-containing material to a value of from about 5 to about 7 to form a neutralized phosphatide mixture; and drying the neutralized phosphatide mixture for a time sufficient to convert the neutralized phosphatide mixture into a vapor phase and a dried phosphatide containing hydrolyzed lecithin.

Still another embodiment of the invention is a process for treating an organic acid-treated phosphatide that comprises the steps of providing a phosphatide-containing material selected from the group consisting of a phosphatide-enriched aqueous phase obtained from an organic acid refining process, an organic acid-treated phosphatide phase obtained from an organic acid refining process, or a mixture thereof; allowing the phosphatide-containing material to remain at acidic pH for a time of no more than about 8 hours; adjusting the pH of the phosphatide-containing material to a value of from about 5 to about 7 to form a neutralized phosphatide mixture; bleaching the neutralized phosphatide mixture; and drying the neutralized phosphatide mixture for a time sufficient to convert the neutralized phosphatide mixture into a vapor phase and a dried phosphatide containing hydrolyzed lecithin.

These and other aspects of the invention will become apparent in light of the detailed description below.

DESCRIPTION OF A PREFERRED EMBODIMENT

Phosphatide-containing materials suitable for use in processes of the invention can be obtained from organic acid refining of vegetable oil, as disclosed in pending U.S. application Ser. No. 09/514,838 and U.S. patent application Ser. No. 09/197,953, herein incorporated by reference in their entirety.

Figure 1:
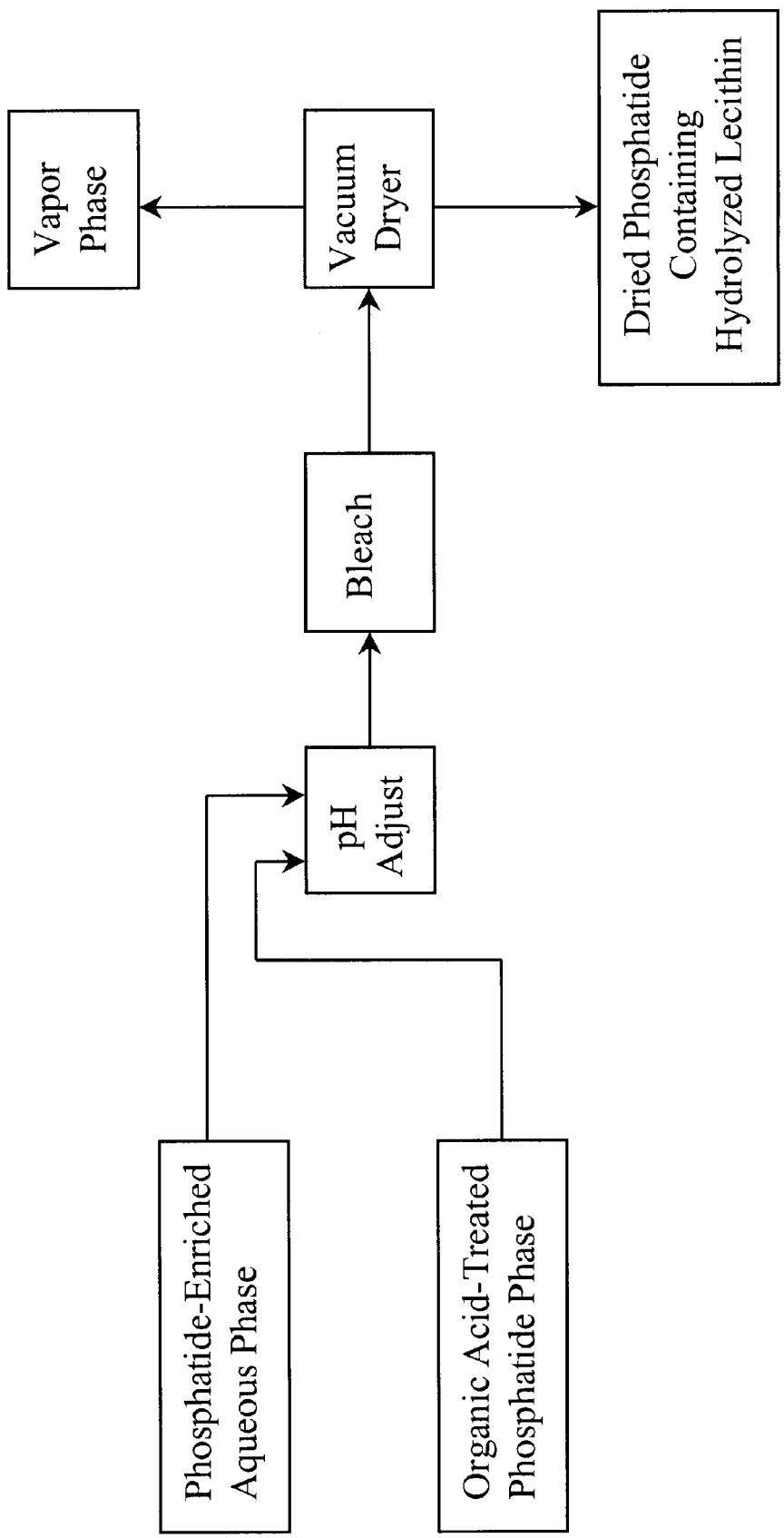
FIG. 1 is a block diagram depicting one process of the invention.

As illustrated in the block diagram of FIG. 1, the invention generally entails providing a phosphatide-containing material; optionally but preferably allowing the phosphatide-containing material to remain at acidic pH for a certain time; adjusting the pH; optionally but preferably bleaching; and drying to form a dried phosphatide containing hydrolyzed lecithin. Once formed, the dried phosphatide can be discharged and sold. The improved processes of the invention for treating phosphatide-containing materials can be conducted as batch or continuous processes.

The improved processes disclosed herein begin by providing a phosphatide-containing material selected from the group consisting of a phosphatide-enriched aqueous phase obtained from an organic acid refining process, an organic acid-treated phosphatide phase obtained from an organic acid refining process, or a mixture thereof. Preferred phosphatide-containing materials are those resulting from citric acid refining of soybean oil.

A phosphatide-enriched aqueous phase generally comprises water, organic acid, and an organic acid-treated phosphatide which itself comprises hydratable phosphatides and nonhydratable phosphatides that have been converted into water-soluble form. A phosphatide-enriched aqueous phase typically comprises from about 30 to about 70 percent by weight water and has a pH of from about 2 to about 4.

An organic acid-treated phosphatide phase generally comprises water, hydratable phosphatides, and nonhydratable phosphatides that have been converted into water-soluble form. An organic acid-treated phosphatide phase typically comprises from about 20 to about 50 percent by weight water and has a pH of from about 2.5 to about 3. Thus, an organic acid-treated phosphatide is more concentrated than a phosphatide-enriched aqueous phase, and accordingly requires less drying time in producing dried phosphatides therefrom. When the phosphatide-containing material comprises a mixture of a phosphatide-enriched aqueous phase and an organic acid-treated phosphatide phase, the two phases can be combined in any ratio. Generally, however, in such mixtures the organic acid-treated phosphatide phase predominates. Either or both of the phases can be supplied from storage or can be supplied as a continuous output stream of an organic acid refining process. Similarly, either or both of the phases can have been allowed to remain at acidic pH for a certain amount of time prior to being provided to the processes of the invention.

After providing the phosphatide-containing material, the pH is adjusted to a value of from about 5 to about 7 to form a neutralized phosphatide mixture. Generally, an aqueous solution of any convenient pH-basic ingredient is used to adjust pH. Such pH-basic ingredients include but are not limited to NaOH and KOH. Preferably, however, the pH-basic ingredient is a food-grade ingredient. One preferred pH-basic ingredient is a 24% aqueous NaOH solution.

The pH-basic ingredient is added in an amount sufficient to adjust pH to a value of from about 5 to 7. Although the weight amount of pH-basic ingredient required will vary depending on the identity (and thus initial pH) of the phosphatide-containing material, generally from about 5 to about 10 percent by weight of a 24% aqueous NaOH solution is required when the phosphatide-containing material is a phosphatide-enriched aqueous phase. Similarly, from about 4 to about 5 percent by weight of a 24% aqueous NaOH solution is typically required when the phopshatide-containing material is an organic acid-treated phosphatide phase.

The pH adjustment can occur either in an agitated holding vessel, such as a low shear mixer, or it can occur in-line, as for example by use of a static mixer. Static mixers are tubular structures having fixed interior mixing elements which simultaneously divide flow and provide high intensity radial mixing. Such mixers are available under the tradenames Kenics Static Mixer, Komax Motionless Blender, Lightnin Series 50 In-Line Blender, Ross Motionless Mixer, and Sulzer Static Mixer.

When pH adjustment occurs in an agitated holding vessel, the phosphatide-containing material and the pH-basic ingredient can be added simulaneously or in any order. A preferred low shear mixer is a 250 or 500 gallon Retention Mixer available from Alfa Laval. When pH adjustment occurs by use of a static mixer, the phopshatide-containing material and the pH-basic ingredient can be combined either upstream of or at the static mixer. A preferred static mixer is Kenics Static Mixer available from Chemineer.

Once pH is adjusted to the desired level, the neutralized phosphatide mixture is optionally but preferably bleached prior to being dried. In a bleaching step, impurities contributing color are removed by action of hydrogen peroxide. Commercial unbleached fluid lecithin has a Gardner color of about 16, while single-bleached material has a Gardner color of about 13. Single bleaching of lecithin generally involves adding 0.25 to 1.5 percent by weight of 30% aqueous $H_2O_2$ to fluid lecithin.

Finally, the neutralized phosphatide mixture or the bleached neutralized phosphatide mixture is dried for a time sufficient to convert it into a vapor phase and a dried phosphatide containing hydrolyzed lecithin. Drying can occur by any convenient mode.

The neutralized phosphatide mixture generally contains from about 25 to about 65 percent by weight water, depending on whether it is derived from a phosphatide-enriched aqueous phase, an organic acid-treated phosphatide phase, or a mixture thereof. This water must be rapidly removed to reduce risk of microbial contamination. In addition to removing water, however, the drying step also removes residual peroxide introduced in bleaching.

Refiners throughout the world typically use one of two types of dryers. One type, vacuum batch dryers, operate at a vacuum in the range of from about 27 to about 29 inches of water and are equipped with rotating ball-shaped coils through which water circulates to maintain a drying temperature of 140–160° F. This type of dryer is less apt to char the lecithin; however, residence times are generally 3 to 5 hours, which can cause objectionable volatile components to become fixed on the lecithin. The other type of dryer, an agitated-film or thin-film evaporator, is much more prevalent, particularly in the United States. Thin film evaporators operate at a vacuum of from about 29 inches of water to about 2 mm Hg and a temperature of 175–225° F. Residence times with this type of dryer are generally minimal, with 1 to 2 minutes being typical. Although thin film evaporators that operate on either a vertical or a horizontal axis are available, the horizontal type is preferred because the lecithin film is much less likely to break.

Either a batch-type or a continuous drying process will suffice, but continuous drying is preferred. More preferred is a continuous agitated-film dryer. Most preferably, drying occurs on a thin-film dryer such as a Votator Turba Fil available from L.C.I. Corp. Advantageously, the neutralized phosphatide mixture is heated to a temperature of from about 120° F. to about 140° F. prior to being introduced into the dryer.

Drying parameters are crucial in producing a dried phosphatide having consumer-preferred odor and flavor. The neutralized phosphatide mixture preferably must be dried down to less than about 0.5 percent by weight water. In order to minimize inducing heat damage to the phosphatides and the danger of chemically fixing objectionable volatile compounds to the lecithin, it is preferred not to exceed a temperature of about 150° F. Even at this temperature, it is preferred to minimize the amount of time the neutralized phosphatide mixture experiences elevated temperature. For these reasons, drying under reduced pressure is preferred.

Reduced pressure can be generated by any convenient source. Steam jet ejector systems are commonly employed. Most preferred is to use a Nash-Kinema three-stage vacuum system or a two-stage vacuum system plus a vacuum pump. Reducing pressure allows a given amount of volatile compounds to be removed at a lower temperature and in a shorter period of time. The dryer therefore preferably operates at a temperature of from about 120° F. to about 150° F. and a pressure of from about 2 to about 50 mm Hg. More preferred is to operate the dryer at a temperature of from about 120° F. to about 140° F. and at a pressure of from about 5 to about 20 mm Hg. Most preferably, the dryer operates at a temperature of from about 120° F. to about 140° F. and a pressure of from about 2 to about 10 mm Hg.

During drying, steam is advantageously contacted with the neutralized phosphatide mixture in the dryer. The steam has a sufficiently high temperature to vaporize objectionable volatile compounds at the dryer operating pressure. In addition to providing a source of heat, steam also helps carry away the vaporizing objectionable volatile compounds. Preferably, the steam has a temperature of from about 200° F. to about 366° F. and a pressure of about 10 to about 150 psig.

Steam is contacted with the neutralized phosphatide mixture via a sparging apparatus. Several steam sparging designs are suitable, the most basic of which consists of pipes submerged within the heated phosphatide concentrate and containing drilled holes for admitting steam into the heated phosphatide concentrate. In another suitable sparging configuration, the internal surface area of the dryer is perforated by a plurality of holes that allow admitting steam into a thin film of neutralized phosphatide mixture traveling along the internal walls. Although the temperature of the admitted steam generally exceeds 150° F., the amount of steam used and the time for which the steam contacts the neutralized phosphatide mixture is kept low to ensure that the steam does not increase the temperature of the neutralized phosphatide mixture above about 150° F. Regulating the heated neutralized phosphatide mixture to a temperature of less than about 150° F. minimizes the risk of fixing objectionable volatile compounds onto the lecithin. Because the dryer operates at reduced pressure and a temperature of less than about 150° F., it produces dried phosphatide by evaporating water. Steam action combines with the action of the evaporating water, providing additional motive force to speed removal of objectionable volatile compounds as they vaporize while the lecithin dries.

The neutralized phosphatide mixture remains in the dryer for a time sufficient to allow the neutralized phosphatide mixture to be dried down to a dried phosphatide having less than about 0.5 percent by weight water. The amount of drying time required to achieve this low level of residual moisture will vary depending on the identity of the phosphatide-containing material from which the neutralized phosphatide mixture is derived. Generally, however, less than about 1 minute of drying at the operating conditions is required to achieve this amount of moisture reduction. Most preferably, the required minimized level of moisture is reached in less than about 30 seconds. Generally, steam is used in amount of less than about 3 percent by weight based on the weight of the neutralized phosphatide mixture. The resulting dried phosphatide is advantageously discharged from the dryer at a temperature of no more than about 150° F., an important consideration again being to minimize inducing heat damage to the now-dried phosphatide.

The dried phosphatide of the invention contains both hydratable phosphatides and non-hydratable phosphatides that have been converted into water-soluble form. Prior methods for recovering dried lecithin have generally produced a maximum amount of only about 45 percent by weight of the phosphatide mixture introduced into the dryer. Such dried lecitihins lacked the non-hydratable phosphatide fraction, either because it was destroyed in earlier processing steps, as for example by formation of soapstock in alkali refining, or because the refining method selected, such as physical refining, could not remove the NHPs. By contrast, processes of the invention recover the nonhydratable as well as hydratable phosphatide fraction. Accordingly, the invention generally produces dried phosphatide in an amount of about 55 percent by weight of the neutralized phosphatide mixture introduced into the dryer.

The dried phosphatide produced by the invention also contains hydrolyzed lecithin. Hydrolyzed lecithin is produced by processes of the invention via acid hydrolysis that causes fatty acid moieties to be cleaved from the glyceride backbone of the phosphatide when the phosphatide-containing material is allowed to remain at acidic pH for a certain time prior to being neutralized. Thus, the amount of hydrolyzed lecithin in the dried phosphatide will vary, with less occurring when the phosphatide-containing material is neutralized immediately as compared to when the phosphatide-containing material is allowed to experience acidic pH for a certain amount of time prior to being neutralized.

Because organic acid is employed, the acid hydrolysis reaction occurs less rapidly and hence can be more easily halted at a particular point as compared to other known processes for producing hydrolyzed lecithin which employ strong acid or base. Accordingly, processes of the invention allow easier control of the acid hydrolysis reaction, and are more amenable to producing a hydrolyzed lecithin in which only one of the fatty acid moieties has been cleaved from the glyceride backbone of the phosphatide. Generally, the dried phosphatide contains at least about 5 percent by weight hydrolyzed lecithin, which results when the phosphatide-containing mixture is allowed to remain at a pH of about 3 for a time of about 6 hours prior to being neutralized.

Figure 2:
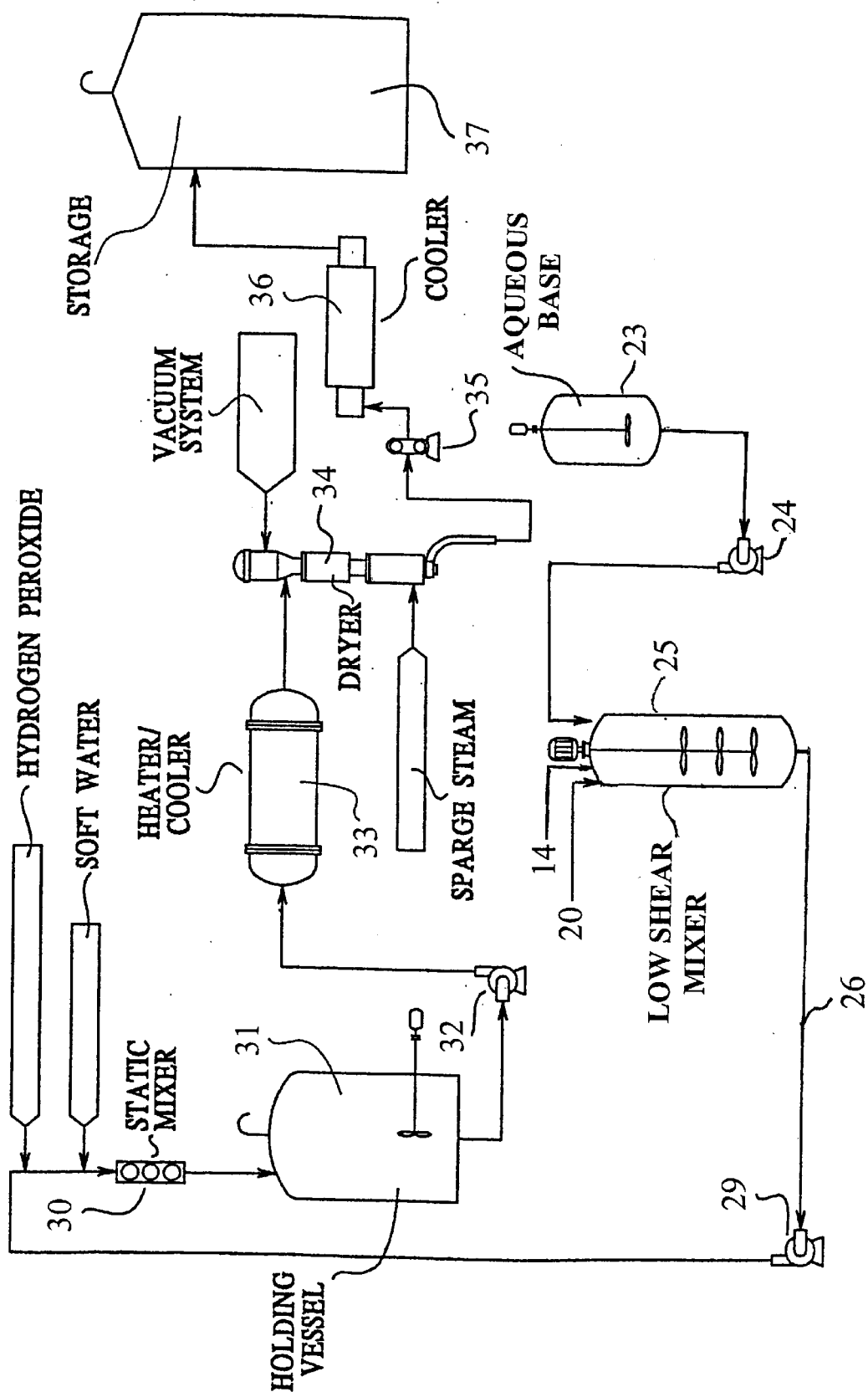
FIG. 2 is a process flow scheme suitable for carrying out one embodiment of the invention.

As illustrated in FIG. 2, in one preferred embodiment of the present invention, a phosphatide-containing material comprising a phosphatide-enriched aqueous phase 14, an organic acid-treated phosphatide phase 20, or a mixture thereof, is combined in a low shear mixer 25 with a 24% aqueous NaOH solution to produce a neutralized phosphatide mixture 26. The 24% aqueous NaOH solution is supplied from a holding vessel 23 via pump 24 and is employed in an amount sufficient to adjust the pH of the phosphatide-containing material to a value of from about 6 to about 7. The phosphatide-containing material is allowed to remain at acid pH for a time of about 8 hours prior to being neutralized in order to produced a desirable amount of hydrolyzed lecithin.

Thereafter, the neutralized phosphatide mixture 26 is withdrawn via pump 29, past which $H_2O_2$ is combined with the neutralized phosphatide mixture. The $H_2O_2$ is preferably added as a 0.2 to 0.5 percent by weight aqueous solution. The $H_2O_2$ is used in an amount of from about 0.1 to about 0.7 percent by weight of neutralized phosphatide mixture.

The combined neutralized phosphatide mixture and $H_2O_2$ is passed through a static mixer 30 to form a bleached neutralized phosphatide mixture. The bleached neutralized phosphatide mixture is fed to a holding vessel 32, then pumped to a heat exchanger 33 via pump 32, wherein the bleached neutralized phosphatide mixture is heated to a temperature of from about 120° F. to about 140° F. to form a heated neutralized phosphatide mixture.

The heated neutralized phosphatide mixture is then pumped to a dryer 34, which is a Votator Turba Film available from L.C.I. Corp. The dryer 34 operates at a temperature of from about 145° F. to about 160° F. and a pressure of about 2 mm Hg. During drying, steam is contacted with the heated neutralized phosphatide mixture in the dryer 34. The heated phosphatide concentrate remains in contact with steam in dryer 34 for a time of about 2 minutes to produce a vapor phase and a dried phosphatide containing no more than about 0.5 percent by weight water.

The resulting dried phosphatide discharges from dryer 34 at a temperature of no more than about 150° F. Thereafter, the dried phosphatide is fed to a cooling unit 36 via pump 35, wherein the dried phosphatide is reduced to a temperature of about 110° F. to about 120° F. The dried phosphatide is then sent to a storage tank 25. The dried phosphatide contains at least about 5 percent by weight hydrolyzed lecithin.

All documents, e.g., patents, journal articles, and textbooks, cited above or below are hereby incorporated by reference in their entirety.

One skilled in the art will recognize that modifications may be made in the present invention without deviating from the spirit or scope of the invention. The invention is illustrated further by the following examples, which are not to be construed as limiting the invention in spirit or scope to the specific procedures or compositions described therein.

EXAMPLE 1

A phosphatide-enriched aqueous phase obtained via citric acid refining of soybean oil, and containing about 70 percent by weight water and with a pH of about 3, was allowed to remain at acid pH for about 6 hours. A 24% aqueous NaOH solution was then admixed in a ratio of 1:10 with the phosphatide-enriched aqueous phase in a low shear mixer. The resulting neutralized phosphatide mixture was introduced into a dryer operating at a temperature of 150° F. and a pressure of 2 mm Hg. The neutralized phosphatide mixture was contacted with steam having a temperature of 194° F. and a pressure of 10 psig and used in an amount of 0.5 percent by weight of neutralized phosphatide concentrate. The neutralized phosphatide concentrate remained in contact with the steam in the dryer for 30 seconds. The resultant dried phosphatide was recovered in an amount of 30 percent by weight of neutralized phosphatide concentrate, and had the characteristics shown in Table 3.

EXAMPLE 2

An organic acid-treated phosphatide phase obtained via citric acid refining of soybean oil, which contained about 25 percent by weight water and had a pH of about 3, was allowed to remain at acid pH for about 6 hours. A 24% aqueous NaOH solution was then admixed in a ratio of 1:20 with the organic acid-treated phosphatide phase in a low shear mixer. The resulting neutralized phosphatide mixture was introduced into a dryer operating at a temperature of 15° F. and a pressure of 2 mm Hg. The neutralized phosphatide mixture was contacted with steam having a temperature of 194° F. and a pressure of 10 psig and used in an amount of 0.5 percent by weight of neutralized phosphatide concentrate. The neutralized phosphatide concentrate remained in contact with the steam in the dryer for 30 seconds. The resultant dried phosphatide was recovered in an amount of 75 percent by weight of neutralized phosphatide concentrate, and had the characteristics shown in Table 3.

TABLE 3

|  | Dried Phosphatide of Example 1 wt % | Dried Phosphatide of Example 2 wt % |
| --- | --- | --- |
| Phosphatidylcholine | 16 | 14 |
| Phosphatidylethanolamine | 14 | 20 |
| Phosphatidylinositol | 9 | 9 |
| Phosphatidic acid | 5 | 14 |
| Hydrolyzed lecithin (LPC) | 5 | 6 |

The invention and the manner and process of making and using it, are now described in such full, clear, concise and exact terms as to enable any person skilled in the art to which it pertains, to make and use the same. Although the foregoing describes preferred embodiments of the present invention, modifications may be made therein without departing from the spirit or scope of the present invention as set forth in the claims. To particularly point out and distinctly claim the subject matter regarded as invention, the following claims conclude this specification.

What we claim is:

1. A process for treating a phosphatide-containing material, comprising:

(a) providing a phosphatide-containing material selected from the group consisting of a phosphatide-enriched aqueous phase obtained from an organic acid refining process, an organic acid-treated phosphatide phase obtained from an organic acid refining process, or a mixture thereof;

(b) adjusting the pH of the phosphatide-containing material to a value of from about 5 to about 7 to form a neutralized phosphatide mixture; and (c) drying the neutralized phosphatide mixture for a time sufficient to convert the neutralized phosphatide mixture into a vapor phase and a dried phosphatide containing hydrolyzed lecithin.

2. The process of claim 1, wherein step (c) drying is by introducing the neutralized phosphatide mixture into a dryer utilizing an operating pressure of less than about 2 mm Hg and a drying temperature of less than about 150° F.

3. The process of claim 2 further comprising step (d) discharging the dried phosphatide at a temperature of less than about 150° F.

4. The process of claim 1, further comprising the step of bleaching the neutralized phosphatide mixture prior to drying.

5. The process of claim 1, further comprising the step of allowing the phopshatide-containing material to remain at acidic pH for a time of no more than about 6 hours prior to being neutralized.

6. The process of claim 5, further comprising the step of bleaching the neutralized phosphatide mixture prior to drying.

7. The process of claim 1, wherein step (c) drying time is no more than about 2 minutes.

8. The process of claim 1, wherein the amount of dried phosphatide produced is greater than about 45 percent by weight of the neutralized phosphatide mixture.

9. The process of claim 1, wherein the dried phosphatide contains at least about 6 percent by weight hydrolyzed lecithin.

10. The process of claim 6, wherein the dried phosphatide contains at least about 5 percent by weight hydrolyzed lecithin.

* * * * *